(12) United States Patent
Lui et al.

(10) Patent No.: US 8,203,015 B2
(45) Date of Patent: Jun. 19, 2012

(54) PROCESS FOR PREPARING FLUOROALKYL NITRILES

(75) Inventors: Norbert Lui, Odenthal (DE); Jens-Dietmar Heinrich, Burscheid (DE); Thomas Wollner, Köln (DE); Sergii Pazenok, Solingen (DE)

(73) Assignee: Bayer Cropscience AG, Monheim (DE)

( * ) Notice: Subject to any disclaimer, the term of this patent is extended or adjusted under 35 U.S.C. 154(b) by 194 days.

(21) Appl. No.: 12/795,168

(22) Filed: Jun. 7, 2010

(65) Prior Publication Data
US 2010/0312002 A1    Dec. 9, 2010

(30) Foreign Application Priority Data

Jun. 8, 2009 (EP) .................................. 09162172

(51) Int. Cl.
*C07C 253/06* (2006.01)

(52) U.S. Cl. ...................................................... 558/313
(58) Field of Classification Search .................. 558/313
See application file for complete search history.

(56) References Cited

PUBLICATIONS

Marshall H. Parker, A Convenient Preparation of Trifluoroacetonitrile: Application to the Synthesis of a Novel Pyrimidinone Building Block, 2004, Synthetic Communications, vol. 34, No. 5, pp. 903-907.*

* cited by examiner

*Primary Examiner* — Kamal Saeed
*Assistant Examiner* — Kristin Bianchi
(74) *Attorney, Agent, or Firm* — Sterne, Kessler, Goldstein & Fox PLLC

(57) ABSTRACT

The present invention relates to a process for preparing fluoroalkyl nitriles by reacting fluorinated carboxamides with halides and fluorinated carboxylic acids.

9 Claims, No Drawings

PROCESS FOR PREPARING FLUOROALKYL NITRILES

The present invention relates to a process for preparing fluoroalkyl nitriles proceeding from fluoroalkylcarboxamides.

Fluoroalkyl nitriles are important intermediates for preparing active agrochemical ingredients.

U.S. Pat. No. 2,939,878 discloses that fluoronitriles can be obtained proceeding from chlorodifluoromethane and cyanogen chloride at temperatures of 500-750° C. The unselective reaction leads to mixtures of trifluoroacetonitrile, chlorodifluoroacetonitrile, 2-chlorotetrafluoropropionitrile and further fluorinated low boilers.

A further patent application (JP 59118751 A) describes the reaction of chlorofluoralkanes of the formula $RFCCl_3$ with ammonia at temperatures of 800° C. The same process is described by Hellberg and Massonne (Chemiker-Ztg./Chem. Apparatur/Verfahrenstechnik, Volume 93 (1969) 6, 209-211). R 113a is reacted with ammonia at 500-800° C. Here too, a mixture of products is obtained ($CF_3CN$, $CF_3Cl$, $CF_3H$, $CF_3CCl_3$, $C_2F_4Cl_2$, $C_2F_2Cl_4$, $C_2F_3Cl$, $CF_2Cl_2$).

Grunewald et al. (J. Med. Chem. 2006, 49, 2939-2952) and also Swarts (Bulletin Societes Chemiques Belges, 1922, Vol 31, 364-365) describe the preparation of difluoroacetonitrile proceeding from difluoroacetamide with phosphorus pentoxide. This involves heating the two solids and condensing the volatile nitrile at −78° C. However, the solid reaction residue which remains in the reaction vessel is difficult to remove.

A further process describes the electrochemical fluorination of acetonitriles (Masatake Haruta and Nobuatsu Watanabe, J. Fluorine Chemistry, 7 (1976)159-177). The reaction proceeds unselectively, and mixtures of reaction products are obtained here too.

Foulletier (EP 55651 B1) describes the gas phase fluorination of trichloroacetonitrile at 400° C. Here too, mixtures are obtained.

Parker describes, in Synthetic Communications (Volume 34, 2004, Pages 903-907) the preparation of trifluoroacetonitrile proceeding from trifluoroacetamide with trifluoroacetic anhydride in pyridine. A disadvantage in this process is the use of expensive trifluoroacetic anhydride, which has to be used stoichiometrically.

All above-described processes are characterized in that specific apparatuses, very high temperatures, expensive and hazardous reagents are required, and the desired products can be isolated from the product mixtures only by complex isolation.

Proceeding from this prior art, it is an object of the present invention to provide a process for preparing fluorinated alkyl nitriles, which can preferably be performed in a simple and inexpensive manner. The fluorinated alkyl nitriles obtainable by this desired process should preferably be obtained with high yield and high purity. More particularly, the desired process should enable the desired target compounds to be obtained without the necessity of complex purification methods.

The object was achieved in accordance with the present invention by a process for preparing fluoroalkyl nitriles of the general formula (I)

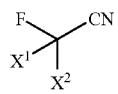
(I)

in which $X^1$ and $X^2$ are each independently fluorine, chlorine, bromine, hydrogen, $C_{1-12}$-alkyl, $C_{1-12}$-haloalkyl, $C_{5-18}$-aryl, $C_{7-19}$-alkylaryl or $C_{7-19}$-arylalkyl, characterized in that fluorinated carboxamides of the formula (II)

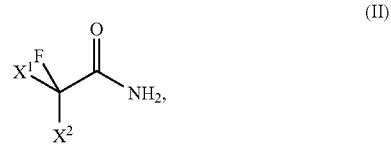
(II)

in which $X^1$ and $X^2$ are each as defined above, in the presence of a base and of catalytic amounts of a fluorinated carboxylic acid of the formula (III)

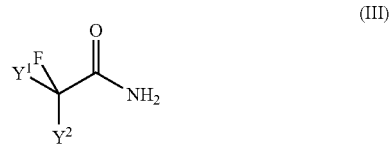
(III)

where $Y^1$ and $Y^2$ are each independently fluorine, chlorine, bromine, hydrogen, $C_{1-12}$-alkyl, $C_{1-12}$-haloalkyl, $C_{5-18}$-aryl, $C_{7-19}$-alkyl aryl or $C_{7-19}$-arylalkyl, are reacted with an acid halide of the formula (IV)

(IV)

in which $R^1$ is $C_{1-12}$-alkyl, $C_{3-8}$-cycloalkyl, $C_{1-12}$-haloalkyl, $C_{5-18}$-aryl, $C_{7-19}$-arylalkyl or $C_{7-19}$-alkylaryl, and Hal is halogen.

Preferred, particularly preferred and very particularly preferred definitions of the $X^1$ and $X^2$ radicals shown in the abovementioned general formula (I) are elucidated hereinafter.

$X^1$ and $X^2$ are preferably each independently fluorine, chlorine, hydrogen, $C_{1-12}$-alkyl, $C_{1-12}$-haloalkyl or $C_{5-18}$-aryl, $X^1$ and $X^2$ are more preferably each independently fluorine, chlorine, hydrogen or $C_{1-12}$-haloalkyl, $X^1$ and $X^2$ are most preferably each independently fluorine, hydrogen or $C_{1-12}$-haloalkyl.

Surprisingly, the fluorinated alkyl nitriles of the formula (I) can be prepared under the inventive conditions with good yields in high purity, by virtue of which the process according to the invention does not have the disadvantages described in connection with the prior art.

The process according to the invention can be illustrated by the following scheme (I):

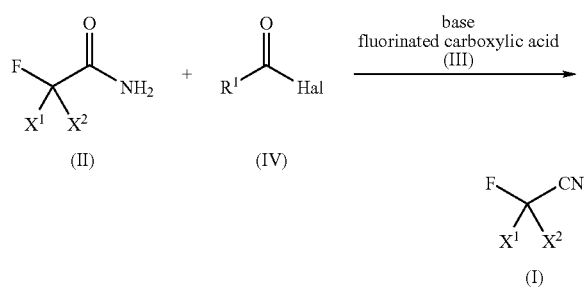

where $X^1$, $X^2$, $R^1$, Hal are each as defined above.
Scheme (I)
General Definitions In connection with the present invention, the term "halogens" (Hal), unless defined otherwise, comprises those elements which are selected from the group consisting of fluorine, chlorine, bromine and iodine, preference being given to using fluorine, chlorine and bromine and particular preference to using fluorine and chlorine.

Optionally substituted groups may be mono- or polysubstituted, where the substituents may be the same or different in the case of polysubstitutions.

Alkyl groups substituted by one or more halogen atoms (-Hal) are, for example, selected from trifluoromethyl ($CF_3$), difluoromethyl ($CHF_2$), $CF_3CH_2$, $ClCH_2$, $CF_3CCl_2$.

In the context of the present invention, unless defined differently, alkyl groups are linear, branched or cyclic saturated hydrocarbon groups.

The definition "$C_1$-$C_{12}$-alkyl" encompasses the largest range defined herein for an alkyl group. Specifically, this definition encompasses, for example, the meanings of methyl, ethyl, n-, iso-propyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In the context of the present invention, unless defined differently, aryl groups are aromatic hydrocarbon groups which may have one, two or more heteroatoms selected from O, N, P and S.

The definition "$C_{5-18}$-aryl" encompasses the largest range defined herein for an aryl group having 5 to 18 framework carbon atoms, where the carbon atoms may be exchanged for heteroatoms. Specifically, this definition encompasses, for example, the meanings of cyclopentadienyl, phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

In the context of the present invention, unless defined differently, alkylaryl groups (aralkyl groups) are alkyl groups which may be substituted by aryl groups and may have a $C_{1-8}$-alkylene chain and may have, in the aryl skeleton, one or more heteroatoms selected from O, N, P and S.

The definition "$C_{7-19}$-aralkyl group" encompasses the largest range defined herein for an arylalkyl group having a total of 7 to 19 atoms in the framework and alkylene chain. Specifically, this definition encompasses, for example, the meanings of benzyl and phenylethyl.

In the context of the present invention, unless defined differently, alkylaryl groups (alkaryl groups) are aryl groups which are substituted by alkyl groups and have a $C_{1-8}$-alkylene chain and may have, in the aryl skeleton, one or more heteroatoms selected from O, N, P and S.

The definition "$C_{7-19}$-alkylaryl group" encompasses the largest range defined herein for an alkylaryl group having a total of 7 to 19 atoms in the framework and alkylene chain. Specifically, this definition comprises, for example, the meanings of tolyl-, 2,3-, 2,4-, 2,5-, 2,6-, 3,4- or 3,5-dimethylphenyl.

Fluorinated Carboxylic Acids (III)

The fluorinated carboxylic acids used according to the present invention are compounds of the general formula (III)

in which
$Y^1$ and $Y^2$ are each independently fluorine, chlorine, bromine, hydrogen, $C_{1-12}$-alkyl, $C_{1-12}$-haloalkyl, $C_{5-18}$-aryl, $C_{7-19}$-alkylaryl or $C_{7-19}$-arylalkyl, preferably hydrogen, fluorine, chlorine, $C_{2-8}$-alkyl or $C_{2-8}$-haloalkyl, more preferably fluorine, chlorine, hydrogen, $C_{3-6}$-alkyl, $CF_3$ or $CF_2H$.

Examples of fluorinated carboxylic acids suitable in accordance with the invention are trifluoroacetic acid, difluoroacetic acid, difluorochloroacetic acid, chlorofluoroacetic acid, 2,3,3,3-tetrafluoropropionic acid, 2,2,3,3-tetrafluoropropionic acid, 2,2-difluoropropionic acid, pentafluoropropionic acid, 2,3,3,4,4,4-hexafluorobutanecarboxylic acid.

The molar ratio of fluorinated carboxylic acid of the formula (III) to the fluorinated alkyl amide of the formula (II) used may, for example, be 0.05 to 1, preferably 0.11 to 0.8, more preferably 0.2 to 0.7. The use of greater amounts (greater molar ratios than 1) of fluorinated carboxylic acid is uncritical but uneconomic.

Acid Halides (IV)

The above-described fluorinated alkyl amides of the formula (II) are converted with addition of an acid halide of the formula (IV).

In formula (IV), $R^1$ is selected from $C_{1-12}$-alkyl, $C_{3-8}$-cycloalkyl, $C_{1-12}$-haloalkyl, $C_{5-18}$-aryl, $C_{7-19}$-arylalkyl or $C_{7-19}$-alkylaryl, preferably from $C_{5-18}$-aryl or $C_{2-8}$-alkyl, more preferably from $C_{3-6}$-alkyl or $C_6$-aryl,
and Hal is fluorine, chlorine, bromine or iodine, preferably chlorine or bromine, more preferably chlorine.

Examples of acid halides suitable in accordance with the invention are acetyl chloride, pivaloyl chloride, 2,2-dimethylbutyryl chloride, isovaleryl chloride and benzoyl chloride.

The molar ratio of acid halides of the formula (IV) to the fluorinated alkyl amide of the formula (II) used may, for example, be 0.5 to 5, preferably 1 to 3, more preferably 2 to 2.5.

Bases

The process according to the invention is performed in the presence of a base. Suitable bases are, for example, substituted or unsubstituted pyridines and substituted or unsubstituted quinolines. Preference is given to using substituted or unsubstituted pyridines and substituted or unsubstituted quinolines.

Preferred examples of bases are pyridine, 3-, 4-picoline, quinoline, quinaldine, halogenated pyridines. Particular preference is given to using pyridine, 4-picoline, 2-chloropyridine.

The molar ratio of base to the fluorinated carboxylic acid of the formula (III) used may, for example, be 0.5 to 10, preferably 1 to 8, more preferably 1.5 to 6.

The use of greater amounts of base is uncritical but uneconomic.

The reaction to prepare the compounds of the general formula (I) can generally be performed under reduced pressure, under standard pressure or under elevated pressure. The temperatures employed can likewise be varied depending on the substrates used and can be determined easily by routine tests by the person skilled in the art. For example, the reaction to prepare the compounds of the general formula (I) can be performed at a temperature of −50 to 250° C., preferably 0 to 170° C. Particular preference is given to performing the reaction at temperatures of 10 to 140° C.

The fluorinated alkyl amides of the formula (II) used in accordance with the present invention are commercially available or can be prepared easily by literature methods (WO 03/080563).

Solvents

The reaction of the fluorinated alkyl amides of the formula (II) to give the compound with the formula (I) can be performed in the presence of a solvent. Preference is given to dispensing with an additional solvent in the reaction. Suitable solvents include: halohydrocarbons and aromatic hydrocarbons, especially chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; ethers such as ethyl propyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylenglycol dimethyl ether, isopropyl ethyl ether, methyl tert-butyl ether, tetrahydrofuran, methyl tetrahydrofuran, dioxane, dichlorodiethyl ether and polyethers of ethylene oxide and/or propylene oxide; nitrohydrocarbons such as nitromethane, nitroethane, nitropropane, nitrobenzene, chloronitrobenzene, o-nitrotoluene; aliphatic, cycloaliphatic or aromatic hydrocarbons such as pentane, n-hexane, n-heptane, n-octane, nonane, for example white spirits with components having boiling points in the range, for example, from 40° C. to 250° C., cymene, petroleum fractions within a boiling range from 70° C. to 190° C., cyclohexane, methylcyclohexane, petroleum ether, ligroin, octane, benzene, toluene, xylene; esters such as methyl acetate, ethyl acetate, butyl acetate, isobutyl acetate, and dimethyl carbonate, dibutyl carbonate, ethylene carbonate. Preferred solvents are toluene or chlorobenzenes.

The desired compounds of the general formula (I) can be isolated, for example, by distillation. In this case, the product (I) can be distilled off simultaneously during the metered addition of the acid chloride of the formula (IV). A further isolation variant is to remove the product of the formula (I) by distillation or filtration only after the end of the reaction.

The present invention is illustrated in detail by the examples which follow, although the examples should not be interpreted in a manner which restricts the invention.

PREPARATION EXAMPLES

Example 1

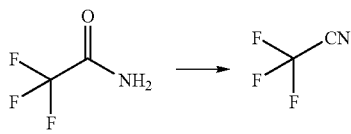

An initial charge of 4.6 g of trifluoroacetic acid in 48.9 g of pyridine is admixed with 13.4 g of trifluoroacetamide. Then 30.4 g of 2,2-dimethylpropanoyl chloride are added dropwise at room temperature to this solution over five hours. The gaseous trifluoroacetonitrile forms immediately in the course of dropwise addition. This can be condensed at relatively low temperatures (e.g. at −100° C.) or introduced directly into a further reaction. The yield is 92%.

Example 2

An initial charge of 2 g of difluoroacetic acid in 34.8 g of pyridine is admixed with 5 g of trifluoroacetamide. Then 10.9 g of 2,2-dimethylpropanoyl chloride are added dropwise at room temperature to this solution over two hours. The gaseous trifluoroacetonitrile forms immediately in the course of dropwise addition. The yield is 90%.

Example 3

An initial charge of 2.4 g of trifluoroacetic acid in 34.8 g of pyridine is admixed with 5 g of trifluoroacetamide. Then 12.4 g of 2,2-dimethylbutyryl chloride are added dropwise at room temperature to this solution over two hours. The gaseous trifluoroacetonitrile forms immediately in the course of dropwise addition. The yield is 84%.

Example 4

An initial charge of 4.6 g of trifluoroacetic acid in 48.9 g of pyridine is admixed with 13.4 g of trifluoroacetamide. Then 35.5 g of benzoyl chloride are added dropwise at room temperature to this solution over five hours. The gaseous trifluoroacetonitrile forms immediately in the course of dropwise addition. The yield is 86%.

Example 5

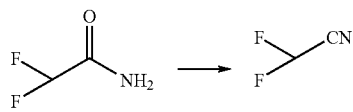

An initial charge of 11.6 g of trifluoroacetic acid in 146.7 g of pyridine is admixed with 19.2 g of difluoroacetamide. Then 51.2 g of 2,2-dimethylpropanoyl chloride are added dropwise at 60° C. to this solution over three hours. Subsequently, the reaction mixture is heated to 100° C. and the difluoroacetonitrile is distilled off. This gives the difluoroacetonitrile in a yield of 88%.

Example 6

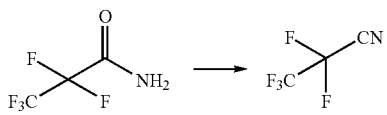

An initial charge of 5.5 g of trifluoroacetic acid in 78 g of pyridine is admixed with 16.1 g of pentafluoropropionamide. Then 24.4 g of 2,2-dimethylpropanoyl chloride are added dropwise at 30° C. to this solution over four hours. The gaseous pentafluoropropionitrile forms immediately in the course of dropwise addition. This can be condensed at relatively low temperatures (e.g. at −80° C.) or introduced directly into a further reaction. The yield is 82%.

The invention claimed is:

1. A process for preparing a compound of the general formula (I),

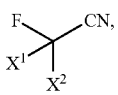

(I)

in which
$X^1$ and $X^2$ are each independently fluorine, chlorine, bromine, hydrogen, $C_{1-12}$-alkyl, $C_{1-12}$-haloalkyl, $C_{5-18}$-aryl, $C_{7-19}$-alkylaryl or $C_{7-19}$-arylalkyl,
comprising, reacting
a fluorinated carboxamide of the formula (II)

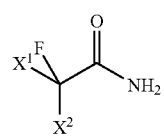

(II)

in which $X^1$ and $X^2$ are each as defined above, in the presence of a base and a catalytic amount of a fluorinated carboxylic acid of the formula (III)

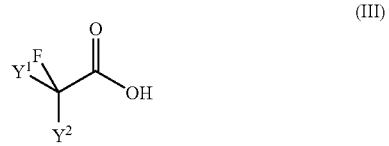

(III)

where
$Y^1$ and $Y^2$ are each independently fluorine, chlorine, bromine, hydrogen, $C_{1-12}$-alkyl, $C_{1-12}$-haloalkyl, $C_{5-18}$-aryl, $C_{7-19}$-alkylaryl or $C_{7-19}$-arylalkyl,
with an acid halide of the formula (IV)

(IV)

in which $R^1$ is $C_{1-12}$-alkyl, $C_{3-8}$-cycloalkyl, $C_{1-12}$-haloalkyl, $C_{5-18}$-aryl, $C_{7-19}$-arylalkyl or $C_{7-19}$-alkylaryl, and Hal is halogen.

2. The process according to claim 1, wherein
$X^1$ and $X^2$ are each independently fluorine, chlorine, hydrogen, $C_{1-12}$-alkyl, $C_{1-12}$-haloalkyl or $C_{5-18}$-aryl,
$Y^1$ and $Y^2$ are each independently hydrogen, fluorine, chlorine, $C_{2-8}$-alkyl or $C_{2-8}$-haloalkyl,
Hal is chlorine or bromine; and
$R^1$ is $C_{2-8}$-alkyl or $C_{5-18}$-aryl.

3. The process according to claim 1, wherein
$X^1$ and $X^2$ are each independently fluorine, chlorine, hydrogen or $C_{1-12}$-haloalkyl,
$Y^1$ and $Y^2$ are each independently fluorine, chlorine, hydrogen, $C_{3-6}$-alkyl, $CF_3$ or $CF_2H$,
$R^1$ is $C_{3-6}$-alkyl or $C_6$-aryl, and
Hal is chlorine.

4. The process according to claim 1, wherein the fluorinated carboxylic acid is selected from the group consisting of trifluoroacetic acid, difluoroacetic acid, difluorochloroacetic acid, chlorofluoroacetic acid, 2,3,3,3-tetrafluoropropionic acid, 2,2,3,3-tetrafluoropropionic acid, 2,2-difluoropropionic acid, pentafluoropropionic acid, and 2,3,3,4,4,4-hexafluorobutanecarboxylic acid.

5. The process according to claim 1, wherein the acid halide is selected from the group consisting of acetyl chloride, pivaloyl chloride, 2,2-dimethylbutyryl chloride, isovaleryl chloride, and benzoyl chloride.

6. The process according to claim 1, where the molar ratio of the fluorinated carboxylic acid of the general formula (III) to the fluorinated carboxamide of the general formula (II) is 0.05 to 1.

7. The process according to claim 1, wherein the molar ratio of the acid halide of the general formula (IV) to the fluorinated carboxamide of the general formula (II) is 0.5 to 5.

8. The process according to claim 1, wherein the base is selected from the group consisting of pyridine, 3-picoline, 4-picoline, quinoline, quinaldine, and a halogenated pyridine.

9. The process according to claim 1, wherein the molar ratio of the base to the fluorinated carboxylic acid of the general formula (III) is 0.5 to 10.

* * * * *